US00RE37473B1

(19) United States
(12) Reissued Patent
Challener

(10) Patent Number: US RE37,473 E
(45) Date of Reissued Patent: Dec. 18, 2001

(54) DIFFRACTION ANOMALY SENSOR HAVING GRATING COATED WITH PROTECTIVE DIELECTRIC LAYER

(75) Inventor: William A. Challener, Grant, MN (US)

(73) Assignee: Imation Corp., Oakdale, MN (US)

(21) Appl. No.: 09/498,758

(22) Filed: Feb. 3, 2000

Related U.S. Patent Documents

Reissue of:
(64) Patent No.: 5,925,878
Issued: Jul. 20, 1999
Appl. No.: 08/915,357
Filed: Aug. 20, 1997

(51) Int. Cl.[7] ..... G02F 1/01
(52) U.S. Cl. ..... 250/225; 356/351; 422/68.1; 250/559.4
(58) Field of Search ..... 250/225, 559.22, 250/559.4; 356/361, 351, 367; 422/68.1, 79, 82.01, 82.09

(56) References Cited

U.S. PATENT DOCUMENTS

| | | | | |
|---|---|---|---|---|
| 4,828,387 | * | 5/1989 | Sawyers | 356/319 |
| 4,877,747 | * | 10/1989 | Stewart | 436/525 |
| 4,882,288 | * | 11/1989 | North | 436/525 |
| 4,931,384 | * | 6/1990 | Layton | 435/7 |
| 4,992,385 | * | 2/1991 | Godfrey | 436/525 |
| 5,071,248 | * | 12/1991 | Tiefenthaler | 356/128 |
| 5,118,608 | * | 6/1992 | Layton | 435/7.1 |
| 5,310,686 | * | 5/1994 | Sawyers | 436/518 |
| 5,365,067 | * | 11/1994 | Cole et al. | 250/341.8 |
| 5,478,755 | * | 12/1995 | Attridge | 436/518 |
| 5,479,260 | * | 12/1995 | Fattinger | 356/361 |
| 5,492,840 | * | 2/1996 | Malmqvist | 436/518 |
| 5,583,643 | * | 12/1996 | Gass | 356/445 |
| 5,598,267 | | 1/1997 | Sambles et al. | 356/369 |
| 5,907,436 | * | 5/1999 | Perry et al. | 359/576 |

FOREIGN PATENT DOCUMENTS

| | | | |
|---|---|---|---|
| 0 321 523 | * | 2/1992 | (EP) . |
| 0 517 930 | * | 12/1992 | (EP) . |
| 0677734 | * | 10/1995 | (EP) . |
| WO92/04617 | * | 3/1992 | (WO) . |
| WO97/09608 | * | 3/1997 | (WO) . |

OTHER PUBLICATIONS

"A Compact Surface Plasmon Resonance Sensor for Measurement of Water in Process", Applied Spectroscopy, R. Matsubara, vol. 42, No. 8, 1998, pp. 1375–1379.*

"A Direct Surface Plasmon–Polariton Immunosensor: Preliminary Investigation of the Non–specific Adsorption of Serum Components to the Sensor Interface", Sensors and Actuators, D.C. Cullen, VI, 1990, pp. 576–579, Jan. 1990.*

(List continued on next page.)

*Primary Examiner*—Que T. Le
(74) *Attorney, Agent, or Firm*—Eric D. Levinson

(57) ABSTRACT

A method and apparatus for optically assaying a targeted substance in a sample using a diffraction anomaly grating sensor. The optical sensor has a diffraction grating coated with at least one dielectric layer such that the sensor is sensitized to interact with the targeted substance. Upon interaction, light incident upon the sensor at a particular angle propagates through the dielectric, thereby exhibiting a dip in zero-order reflectance. Advantages of the present invention include facilitating increased sensitivity while protecting the metal grating from tarnishing and degradation. The present invention also allows for the construction of sensors that are sensitized to a plurality of substances, thus eliminating the need for an operator to reconfigure the sensing system in order to assay different substances.

34 Claims, 3 Drawing Sheets

OTHER PUBLICATIONS

"Choice of Metal and Wavelength for Surface–Plasmon Resonance Sensors: Some Considerations", Applied Optics, Helene E. DeBruijin, vol. 31, No. 4, Feb. 1992.*

"Detection of Amine Gases by Color Changes of Acid–Base Indicators Supported on Inorganic Films", Reports of the Facuty of Engineering Nagasaki University, Yuji Takao, vol. 26, No. 46, Jan. 1996.*

"Detection of Immuno–complex Formation via Surface Plasmon Resonance on Gold–Coated Diffraction Gratings", Biosensors, 3, 1987/88, D.C. Cullen, pp. 211–225, Jan. 1987.*

"Development of a Prototype Gas Sensor Using Surface Plasmon Resonance og Gratings", Sensors and Actuators, M. J. Jory, B, 17, 1994, pp. 203–209, Jan. 1994.*

"Double Excitation of a Resonance Surface Plasmon Maximum", Journal of Modern Optics, M.J. Jory, 1993, vol. 40, No. 9, pp. 1657–1662, Jan. 1993.*

"Gas Detection By Means of Surface Plasmon Resonance", Sensors and Actuators, Claes Nylander, vol. 3, 1982–83, pp. 79–88. Jun. 1982.*

"Grating–Coupled Surface Plasmon for Measuring the Refractive Index of a Liquid Sample", J. Phys. D: Applied Physics, Hiroshi Kano, vol. 34, 1995, pp. 331–335, Jan. 1995.*

"Optimization of a Chemooptical Surface Plasmon Resonance Based Sensor", Applied Optics, Jos van Gent, vol. 29, No. 19, Jul. 1, 1990.*

"Polarisation Conversion Through the Excitation of Surface Plasmons on a Matallic Grating", Journal of Modern Optics, G. P. Bryan–Brown, 1990, vol. 37, No. 7, 1227–1232, Jan. 1990.*

"Properties and Applications of Layered Grating Resonances", SPIE, Application and Theory of Periodic Structures, Diffraction Gratings and More PhenomenaIII, vol. 815, 1987, pp. 158–167, Jan. 1987.*

"Resonance Anomalies in the Light Intensity Reflected at Silver Gratings with Dielectric Coatings", J. Phys. D: Applied Physics, I, Pockrand, vol. 9, 1976, pp. 2423–2432, May 1976.*

"Surface Plasmon Resonance on Gratings as a Novel Means for Gas Sensing", Sensors and Actuators, P.S. Vukusic, B, 8, 1992, pp. 155–160, Jan. 1992.*

"Surface–Resonance Polarization Conversion Mediated By Broken Surface Symmetry", The American Physical Society, Physical Review B, S.J. Elston, vol. 44, No. 7, Aug. 15, 1991–I.*

"Unusual splitting behavior of the dispersion of surface polaritons in grating of different symmetry, amplitude, and profile", Applied Optics, B. Fischer, vol. 34, No. 25, Sep. 1, 1995, pp. 5773–5779.*

"Vector Diffraction of a Grating and Conformal Thin Films", Optical Society of America, W.A. Challener, vol. 13, No. 9, Sep. 1996, pp. 1859–1869.*

* cited by examiner

DIFFRACTION ANOMALY SENSOR HAVING GRATING COATED WITH PROTECTIVE DIELECTRIC LAYER

Matter enclosed in heavy brackets [ ] appears in the original patent but forms no part of this reissue specification; matter printed in italics indicates the additions made by reissue.

FIELD OF THE INVENTION

This invention relates generally to the field of optical sensing and, more particularly, to a method and apparatus for assaying chemical and biological materials.

BACKGROUND OF THE INVENTION

Recently, extremely sensitive optical sensors have been constructed by exploiting an effect known as surface plasmon resonance (SPR). These sensors are capable of detecting the presence of a wide variety of materials in concentrations as low as picomoles per liter. SPR sensors have been constructed to detect many biomolecules including dinitrophenyl, keyhole limpet hemocyanin, α-Feto protein, IgE, IgG, bovine and human serum albumin, glucose, urea, avidin, lectin, DNA, RNA, hapten, HIV antibodies, human transferrin, and chymotrypsinogen. Additionally, SPR sensors have been built which detect chemicals such as polyazulene and various gases including halothane, tricloroethane and carbon tetrachloride.

An SPR sensor is constructed by sensitizing a surface of a substrate to a specific substance. Typically, the surface of the substrate is coated with a thin film of metal such as silver, gold or aluminum. Next a sensitizing layer, such as a monomolecular layer of complementary antigens, is covalently bonded to the surface of the thin film. In this manner, the thin film is capable of interacting with a predetermined chemical, biochemical or biological substance. When an SPR sensor is exposed to a sample that includes the targeted substance, the substance attaches to the sensitizing layer and changes the effective index of refraction at the surface of the sensor. Detection of the targeted substance is accomplished by observing the optical properties of the surface of the SPR sensor.

The most common SPR sensor involves exposing the surface of the sensor to a light beam through a glass prism. At a specific angle of incidence, known as the resonance angle, a component of the light beam's wavevector in the plane of the sensor surface matches a wavevector of a surface plasmon in the thin film, resulting in very efficient energy transfer and excitation of the surface plasmon in the thin film. As a result, at the resonance angle the reflected light from the surface of the sensor exhibits a sharp dip that is readily detected. When the targeted substance attaches to the surface of the sensor, a shift in the resonance angle occurs due to the change in the refractive index at the surface of the sensor. A quantitative measure of the concentration of the targeted substance can be calculated according to the magnitude of shift in the resonance angle.

SPR sensors have also been constructed using metallized diffraction gratings instead of prisms. For SPR grating sensors, resonance occurs when a component of the incident light polarization is perpendicular to the groove direction of the grating and the angle of incidence is appropriate for energy transfer and excitation of the thin metal film. As with prism-based sensors, a change in the amount of light reflected is observed when the angle of incidence equals the resonance angle. Previous SPR grating sensors have incorporated square-wave or sinusoidal groove profiles.

SPR grating sensors offer many benefits over SPR sensors having glass prisms including a thicker, more robust metal film. Furthermore, the grating period for an SPR grating sensor can be adjusted for any desired resonance angle. Despite these benefits, both current SPR grating sensors and prism-based sensors are susceptible to degradation due to oxidation of the metal film and its continuous exposure to the sample. For this reason, the thin metal film is usually constructed with a metal that tarnishes slowly, such as gold, rather than a highly sensitive metal which tarnishes more quickly, such as silver. Another disadvantage of current SPR sensors is that the metal film causes many biological substances to denature, thus leading to erroneous readings. For the reasons stated above, and for other reasons stated below which will become apparent to those skilled in the art upon understanding the present invention, there is a need in the art for an optical sensor having improved sensitivity and less susceptibility to degradation.

SUMMARY OF THE INVENTION

In one aspect, the invention is a sensor for assaying a substance in a sample. The sensor comprises a substrate having a plurality of grooves in a surface. The grooves are formed in a substantially periodic profile such as sinusoidal, trapezoidal or any other suitable formation. A metal layer is formed outwardly from the surface of the substrate. In this manner, the metal layer substantially conforms to the grooved profile of the surface of the substrate. A dielectric layer is formed outwardly from the metal layer and is selected so as to suppress the zero-order reflectance of light polarized parallel to the grooves of the surface for at least one angle of incidence. It is preferable that the dielectric layer has a thickness of at least 50 nm or, more preferably, at least 130 nm.

The sensor may include a sensitizing layer formed outwardly from the dielectric layer. The sensitizing layer is capable of interacting with the substance in the sample and thereby changes the angle of incidence at which the sensor suppresses the zero-order reflectance of incident light. In one embodiment the sensitizing layer comprises a layer of antigens. In another embodiment, the dielectric layer is capable of interacting with the substance in the sample.

In yet another embodiment, the invention is a sensor for assaying a plurality of substances in a sample. The sensor includes a substrate having a surface formed in a substantially periodic grooved profile and a metal layer is formed outwardly from the surface of the substrate. A plurality of substantially non-overlapping dielectric layers are formed outwardly from the metal layer. Each of the dielectric layers is capable of suppressing the zero-order reflectance of incident light for at least one corresponding angle of incidence and polarization. This embodiment facilitates the sensing of a plurality of substances in a sample or the reuse of a single sensor for multiple samples having various substances.

In one aspect, the invention is a method for assaying a substance in a sample using a sensor having a grooved diffraction grating surface coated with a dielectric layer. The sensor is exposed over a plurality of incident angles by a light beam polarized parallel to the grooves in the diffraction grating surface. A controller detects a first diffraction anomaly angle at which zero-order reflectance of a component of the incident light having a polarization parallel to the grooves of the sensor is a minimum. After interacting the sensor with the sample, the sensor is exposed a second time with a light beam over the plurality of incident angles and a second diffraction anomaly angle is detected. A measure of the substance in the sample is determined as a function of the first diffraction anomaly angle and the second diffraction anomaly angle.

DETAILED DESCRIPTION

In the following detailed description, references are made to the accompanying drawings that illustrate specific embodiments in which the invention may be practiced. Electrical, mechanical and structural changes may be made to the embodiments without departing from the spirit and scope of the present invention. The following detailed description is, therefore, not to be taken in a limiting sense and the scope of the present invention is defined by the appended claims and their equivalents.

Figure 1:
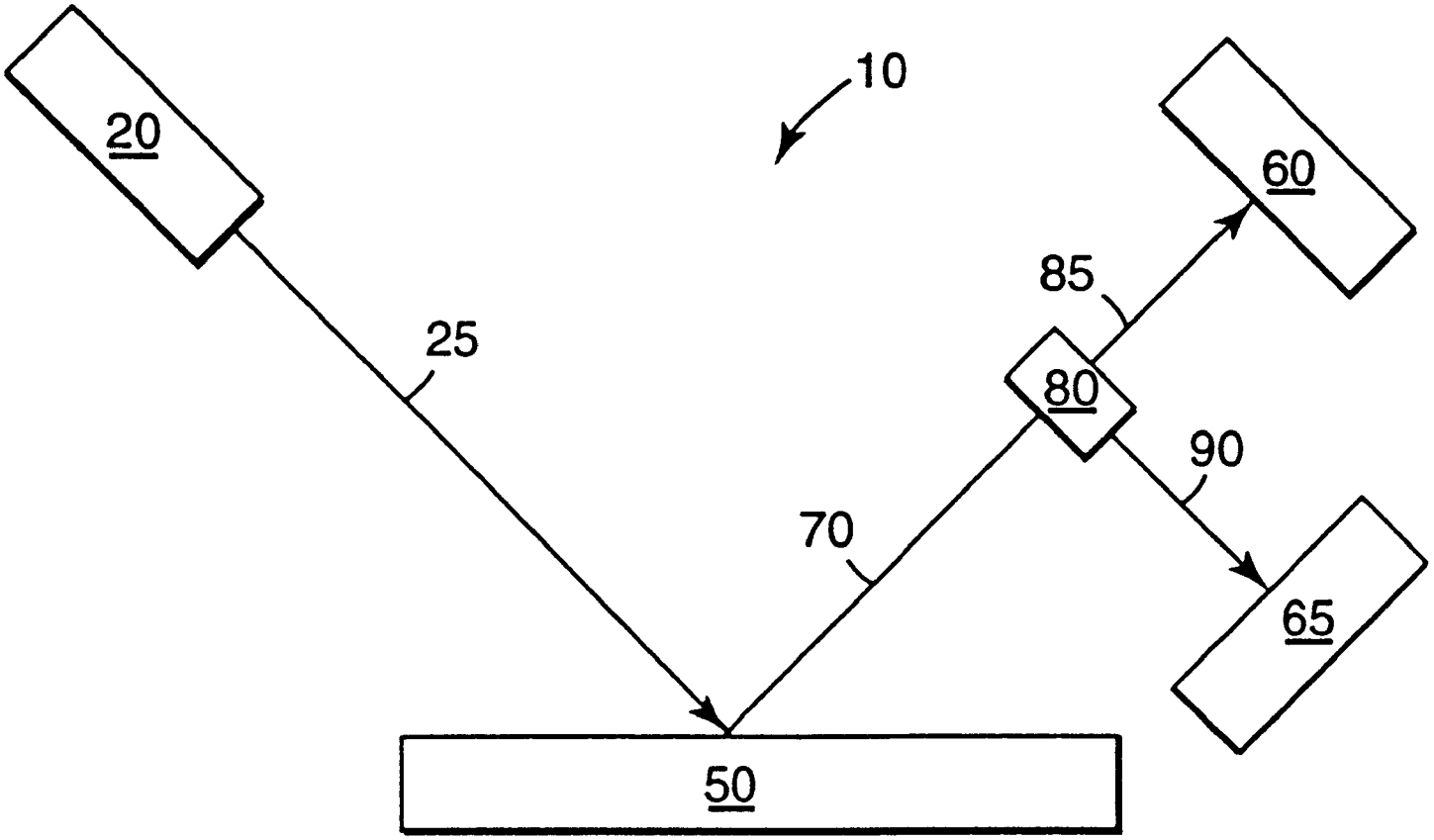
FIG. 1 is a schematic side view of one embodiment of a sensing system that detects a substance by exposing a diffraction anomaly sensor having a dielectric coated metal grating and detecting a shift in the incidence angle that results in minimum reflectivity.

FIG. 1 illustrates a sensing system 10 in accordance with the present invention. Sensing system 10 includes light source 20, diffraction anomaly sensor 50, polarizing beamsplitter 80, detector 60 and detector 65. Light source 20, such as a laser, produces a light beam 25 incident upon sensor 50. Sensor 50 reflects light beam 25 as light beam 70 onto polarizing beamsplitter 80. Polarizing beamsplitter 80 splits light beam 70 into component 85 and component 90 which are incident upon detector array 60 and detector array 65, respectively.

Sensor 50 is a diffraction anomaly sensor having a metal grating that is coated with a dielectric layer as discussed in detail below. Similar to SPR sensors, sensor 50 exhibits a change in reflectivity, referred to as a diffraction anomaly, when exposed with light beam 25 at a particular angle of incidence. Unlike an SPR sensor, however, the change in reflectivity of sensor 50 occurs for light polarized parallel to the grating grooves rather than perpendicular to the grating grooves. In accordance with the present invention, it is observed that the effective index of refraction at the surface of sensor 50 changes in a manner similar to an SPR sensor when sensor 50 is smeared with a sample containing a targeted substance. It is further observed that the change in the index of refraction in turn shifts the incidence angle at which the diffraction anomaly occurs. Furthermore, for a fixed wavelength of light beam 25, the diffraction anomaly angle is strongly dependent upon the amount of targeted substance present in the sample. In this manner, sensor 50 exhibits a shift in the anomaly angle that is comparable to a SPR sensor, even though the metal grating of sensor 50 is coated with a dielectric layer. Therefore, a quantitative measure of the targeted substance can be calculated by measuring the resulting shift in the anomaly angle.

After exposing sensor 50 to the sample, the new anomaly angle for sensor 50 is determined by directing light beam 25 to sensor 50 over a range of incidence angles. In one embodiment, sensor 50 is rotated so as to vary the angle of incidence of light beam 25. In another embodiment, sensor 50 is fixed and light source 20 directs light beam 25 to sensor 50 over a range of incidence angles.

Polarizing beamsplitter 80 splits light beam 70 such that component 85 has a wave vector parallel to the grooves of the surface of sensor 50 and component 90 has a wave vector perpendicular to the grooves of the surface of sensor 50. A controller (not shown) monitors detectors 60 and 65 and continuously ratios the intensities of light component 85 and light component 90 received by detectors 60 and 65. In this manner, light fluctuations of the light source, or other system variations such as ripples in the sample, do not affect the calculation of the targeted species in the sample. Based on the calculated ratio for each sensing element for detector arrays 60 and 65, the controller determines a new diffraction anomaly angle and calculates a measure of the targeted substance in the sample based on the new diffraction anomaly angle. In another embodiment, the controller monitors the diffraction anomaly angle and sounds an alarm when the calculated measure of the targeted substance exceeds a predetermined threshold. After sensing is complete, SPR grating sensor 50 may be disposed or may be washed and reused.

Figure 2:
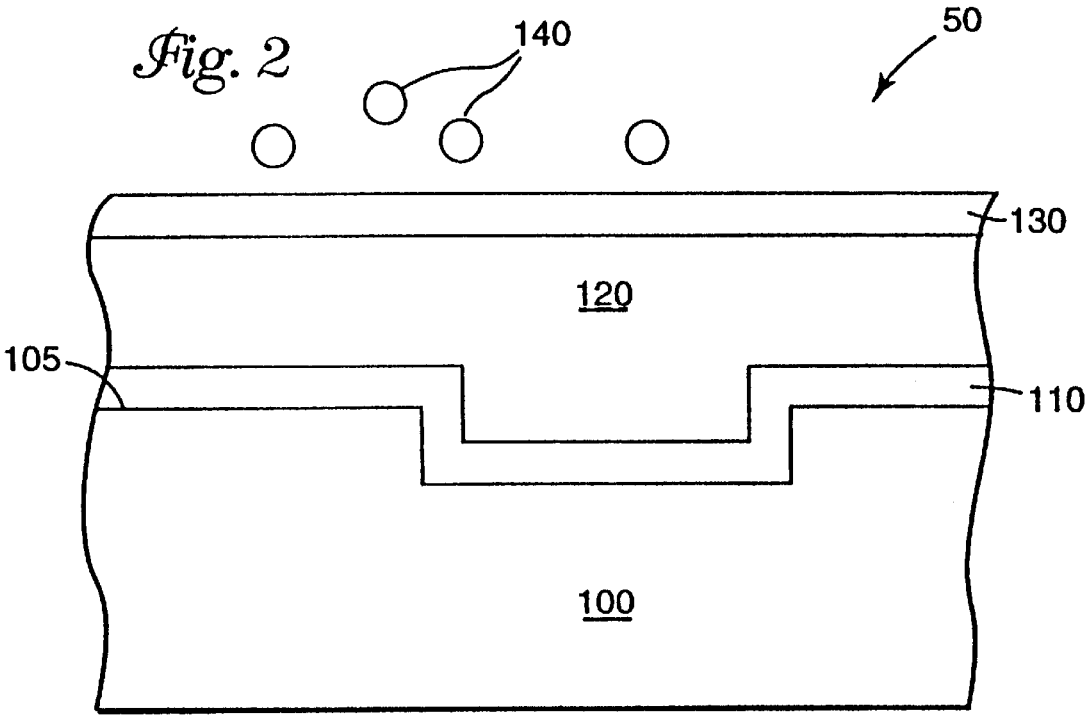
FIG. 2 is a schematic side view of one embodiment of a diffraction anomaly sensor having a dielectric-coated metal grating in accordance with the present invention.

FIG. 2 illustrates in detail one embodiment of diffraction anomaly sensor 50 in accordance with the present invention. Sensor 50 includes substrate 100 having a grooved surface 105. The grooves of surface 105 are periodic and, in one embodiment, have a square cross-sectional shape. Other cross-sectional shapes are contemplated for the grooves of surface 105 including but not limited to sinusoidal, trapezoidal and triangular. The period of the grooves of surface 105 may range from less than 0.4 $\mu$m to over 2.0 $\mu$m.

Thin metal layer 110 is formed outwardly from surface 105 of substrate 100 and comprises any suitable metal such as aluminum, gold or silver. Dielectric layer 120 is formed outwardly from metal layer 110 and thereby protects metal layer 110 from oxidation and general degradation. In this manner, metal layer 110 may comprise any suitable metal and may be selected to optimize sensitivity. In one embodiment, layer 110 comprises silver having a thickness of approximately 100 nm. As is described in detail below, the diffraction anomaly exhibited by sensor 50 is directly affected by the thickness and dielectric constant of dielectric layer 120. Dielectric layer 120 comprises any suitable dielectric material such as silicon nitride, $Si_3N_4$, and is preferably at least 50 nm thick. Alternatively, dielectric layer 120 may have a thickness of at least 100 nm or, more preferably, at least 130 nm.

In one embodiment, sensitizing layer 130 is formed outwardly from dielectric layer 120. Because dielectric layer 120 is disposed between sensitizing layer 130 and metal layer 110, dielectric layer 120 prevents chemical reaction between the metal layer 110 and sensitizing layer 130. Sensitizing layer 130 is selected to interact with a predetermined chemical, biochemical or biological substance 140 contained in the sample. In this manner, sensitizing layer 130 may comprises a layer of antigens capable of trapping a complementary antibody. Recently, several techniques have been developed for attaching antigens to dielectric layer 120 such as by spin coating with a porous silica sol-gel or a hydrogel matrix. Preferably, sensitizing layer 130 is less than 100 nm thick. In another embodiment, dielectric layer 120 is selected so as to interact directly with substance 140, thereby eliminating the need for sensitizing layer 130.

Unlike conventional SPR sensors, diffraction anomaly sensor 50 exhibits a reflectance dip for light polarized parallel to the grooves of surface 105. When light beam 25 has an angle of incidence equal to the diffraction anomaly angle for sensor 50, light beam 70 is not received by detector 60 but propagates within dielectric layer 120. In this manner, dielectric layer 120 acts as a waveguide and the dip in reflectivity is readily detected by the controller.

The following equations can be used to select dielectric layer 120 such that a diffraction anomaly angle, $\theta_{SP}$, occurs for component 85 having a polarization parallel to the grooves of surface 105. Using an iterative process, a wavevector for the diffraction anomaly resonance, $k_x$, can be calculated from the following equation:

$$\left(\varepsilon_1\sqrt{\varepsilon_1 k_0^2 - k_x^2} + \varepsilon_0\sqrt{\varepsilon_0 k_0^2 - k_x^2}\right)\left(\varepsilon_2\sqrt{\varepsilon_2 k_0^2 - k_x^2} + \varepsilon_1\sqrt{\varepsilon_1 k_0^2 - k_x^2}\right) + \left(\varepsilon_1\sqrt{\varepsilon_1 k_0^2 - k_x^2} - \varepsilon_0\sqrt{\varepsilon_0 k_0^2 - k_x^2}\right)\left(\varepsilon_2\sqrt{\varepsilon_2 k_0^2 - k_x^2} - \varepsilon_1\sqrt{\varepsilon_1 k_0^2 - k_x^2}\right)\exp\left(2i\sqrt{\varepsilon_1 k_0^2 - k_x^2}\,d\right) = 0$$

In this equation, $\epsilon_0$ is the dielectric constant of the medium above the substrate, such as air or water, etc., $\epsilon_1$ is the dielectric constant of the dielectric layer, and $\epsilon_2$ is the dielectric constant of the metal film. Furthermore, $k_0$ is a wavevector of the incident light in vacuum and equals $2\pi/\lambda$. Finally, d is the thickness of the dielectric layer.

Once the wavevector for the diffraction anomaly resonance has been found, the following equation can be used to solve for the diffraction anomaly angle, $\theta_{SP}$:

$$\sin\theta_{SP} = -\left(\frac{m\lambda}{n_0 p}\right)\cos\phi_{SP} \pm \sqrt{\left(\frac{k_x}{n_0 k_0}\right)^2 - \left(\frac{m\lambda}{n_0 p}\sin\phi_{SP}\right)^2}.$$

In this equation, $\phi_{SP}$ is the azimuthal angle of incident light beam 25 with respect to the grooves of surface 105, where 0° corresponds to the plane of incidence perpendicular to the groove direction, $n_0$ is the index of refraction of the sample, $\lambda$ is the wavelength of light beam 25, p is the period of the grooves of surface 105, and m is an integer. Thus, a dielectric layer having a suitable dielectric constant may be readily selected so as to suppress component 85 which has a polarization parallel to the grooves in surface 105 of sensor 50.

Figure 3:
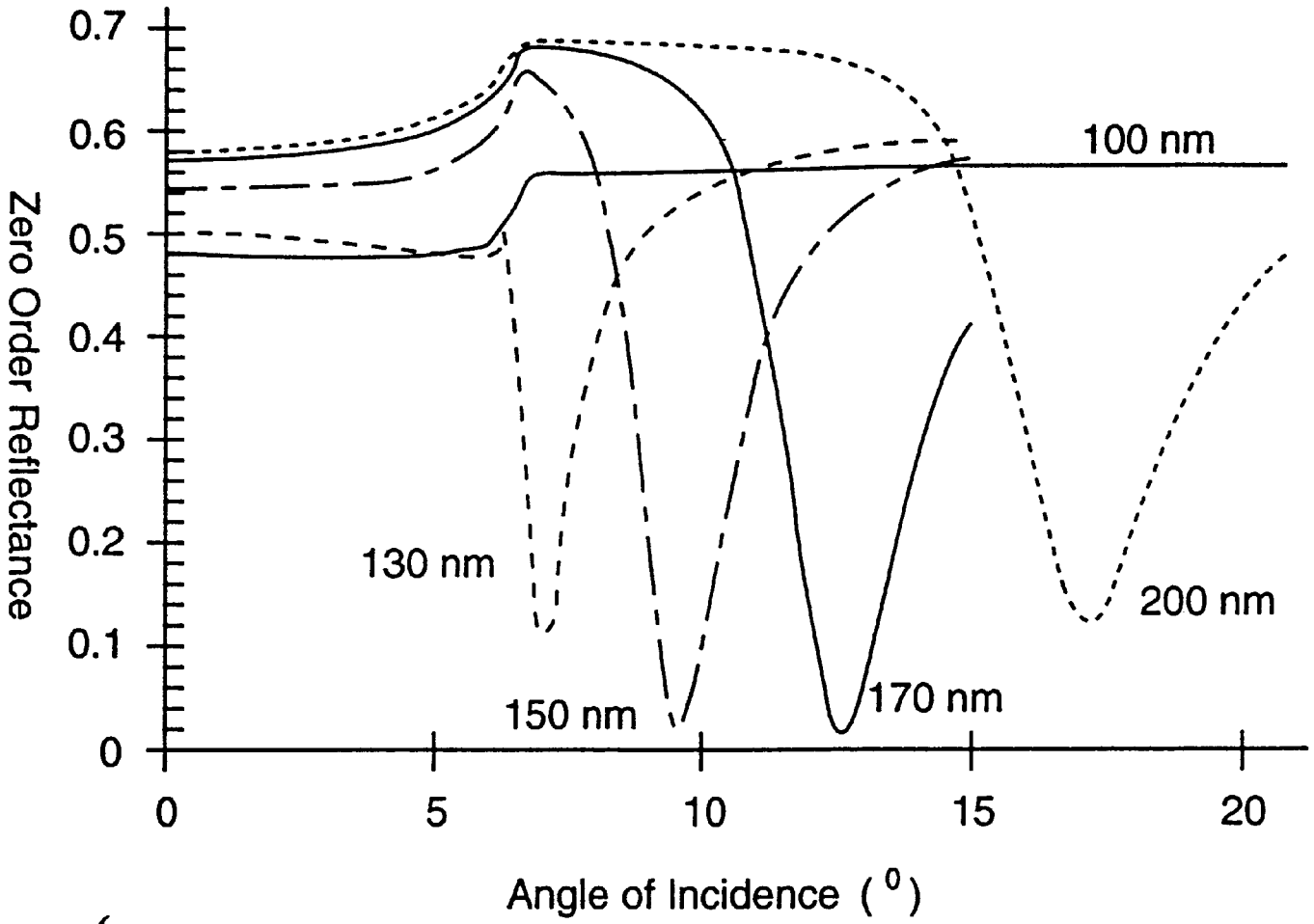
FIG. 3 is a graph that illustrates the calculated zero-order reflectance over angles of incidence ranging from 0° to 20° for several diffraction anomaly sensors having dielectric layers of differing thickness.

FIG. 3 plots the calculated reflectance of sensor 50 over a range of incidence angles for light beam 25. More specifically, the zero-order reflectance of sensor 50 is plotted for incidence angles ranging from 0° (normal) to 20° and an azimuthal angle of 0°. Furthermore, reflectivity is plotted for various thicknesses of dielectric layer 120 of sensor 50. In modeling the reflectivity of sensor 50, a sinusoidal profile for surface 105 was selected having a period of 0.66 $\mu$m and a peak-to-peak amplitude of 0.107 $\mu$m. Metal layer 110 was modeled by selecting optically thick aluminum having an index of refraction of n=2+i8, assuming a wavelength of 780 nm for light beam 25. Furthermore, dielectric layer 120 was modeled by a dielectric having an index of refraction of n=2.

FIG. 3 illustrates that the diffraction anomaly angle shifts as the thickness of dielectric layer 120 is increased. In addition, FIG. 3 is representative of the shifting of the diffraction anomaly angle of sensor 50 due to interaction with the targeted species. Increasing the thickness of dielectric layer 120 represents the increase in thickness of the sensitizing layer as the targeted substance attaches to it, resulting in a shift of the diffraction anomaly angle by approximately 10 degrees.

Figure 4:
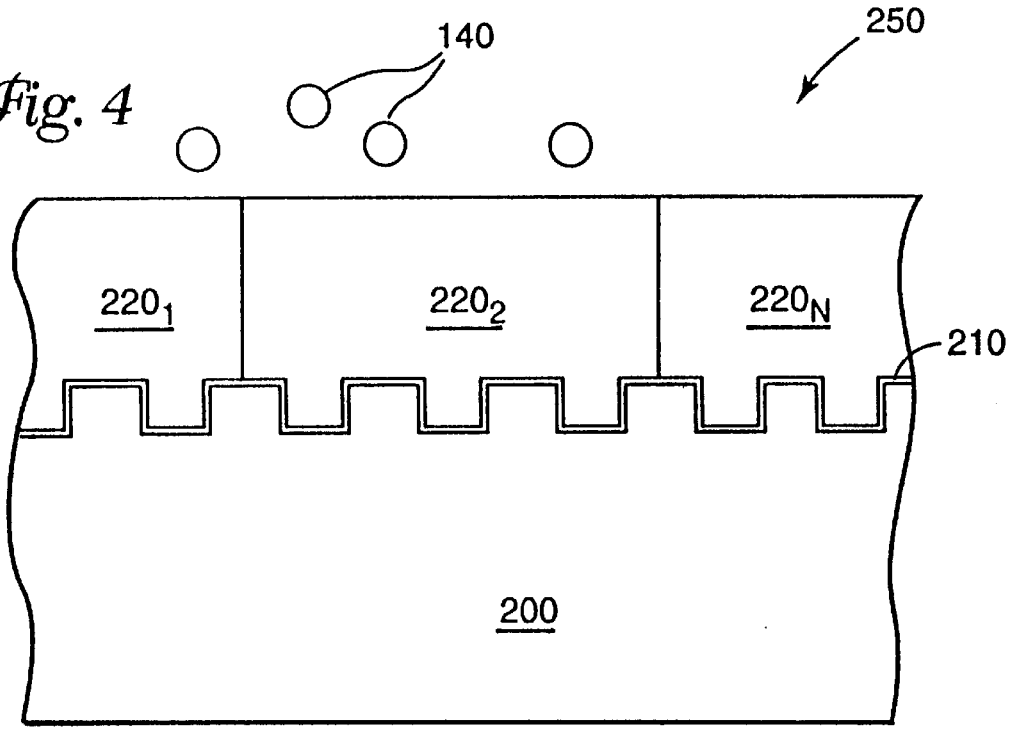
FIG. 4 is a schematic side view of one embodiment of a diffraction anomaly sensor having a plurality of dielectric layers, each dielectric layer substantially sensitized for a different targeted substance.

As described above, dielectric layer 120 may be selected such that it interacts with substance 140 directly, thereby eliminating the need for sensitizing layer 130. This technique is advantageous in that a sensor may be developed that is sensitized to a variety of different substances. FIG. 4 illustrates one embodiment of a diffraction anomaly sensor that is sensitized to interact with a plurality of substances. More specifically, sensor 200 includes substrate 200 having grooves with square cross-sectional profiles. Other cross-sectional profiles are contemplated including sinusoidal, trapezoidal and triangular and the square groove profile is chosen for exemplary purposes only. The period of the grooves in the surface of substrate 200 may range from less than 0.4 $\mu$m to over 2.0 $\mu$m.

Thin metal layer 210 is formed outwardly from substrate 200 and is substantially similar to thin metal layer 110 of FIG. 2. A plurality of dielectric layers $\mathbf{220}_1$ through $\mathbf{220}_N$ are formed along metal layer 210 and are substantially non-overlapping as shown in FIG. 4. Dielectric layers 220 protect metal layer 210 from oxidation and degradation. Each dielectric layer 220 is selected to interact with different chemical, biochemical or biological substance 140 contained in the sample. In this configuration, sensor 200 is sensitized to interact with a variety of substances. One advantage of this configuration is that an operator does not need to reconfigure sensing system 10 in order to assay different substances. Another advantage is that a single sample may be assayed for a plurality of substances simply be interacting sensor 200 with the sample, selectively exposing dielectric layers 220 with an incident light beam and detecting any shift in the corresponding diffraction anomaly angle. The diffraction anomaly exhibited by sensor 200 is directly affected by the thickness and index of refraction of the exposed dielectric layer 220. In one embodiment, dielectric layers 220 have substantially equal thickness of at least 120 nm. In another embodiment, the thickness of dielectric layers 220 varies in order to optimize the sensitivity of sensor 200 to the corresponding substance 140.

CONCLUSION

Various embodiments of a method and system for assaying a substance in a sample using a diffraction anomaly sensor have been described. In one embodiment, the present invention is a sensing system that exposes a diffraction anomaly sensor with a light beam and quantitatively measures the concentration of targeted substance by determining the corresponding diffraction anomaly angle. In another embodiment, the present invention is a diffraction anomaly sensor having a metal diffraction grating coated with a protective dielectric. For a particular angle of incidence, incident light having a polarization component parallel to the grooves within the metal grating propagates through the dielectric layer causing a dip in zero-order reflectance. In another embodiment, the present invention is a diffraction anomaly sensor that is sensitized to interact with a plurality of substances.

Several advantages of the present invention have been illustrated including eliminating the degradation and oxidation of the metal grating of conventional SPR grating sensors. In this manner, the present invention allows the metal grating to be selected so as to optimize the sensitivity of the system. Furthermore, the present invention allows for the construction of sensors that are sensitized to a plurality of substances, thus eliminating the need for an operator to reconfigure the sensing system in order to assay different substances.

This application is intended to cover any adaptations or variations of the present invention. It is manifestly intended that this invention be limited only by the claims and equivalents thereof.

I claim:

1. A sensor for assaying a substance in a sample comprising:

a substrate having a plurality of parallel grooves in a surface;

a metal layer formed outwardly from the surface of the substrate, the metal layer substantially conforming to the grooved surface of the substrate; and a dielectric layer formed outwardly from the metal layer, [the dielectric layer for suppressing reflection of incident light having a polarization parallel to the grooves of the substrate]

*wherein for light having a plane of incidence perpendicular to the grooves of the substrate the dielectric layer suppresses a component of the light having a polarization parallel to the grooves of the substrate*.

2. The sensor of claim 1, further comprising a sensitizing layer formed outwardly from the dielectric layer, wherein the sensitizing layer interacts with the substance in the sample.

3. The sensor of claim 1, wherein the dielectric layer interacts with the substance in the sample.

4. The sensor of claim 1, wherein the dielectric layer has a thickness of at least 50 nm.

5. The sensor of claim 1, wherein the dielectric layer has a thickness of at least 130 nm.

6. The sensor of claim 1, wherein a cross-sectional shape of the grooved surface of the substrate is substantially periodic.

7. The sensor of claim 6, wherein the cross-sectional shape of the grooved surface is selected from the set of sinusoidal, trapezoidal and triangular.

8. The sensor of claim 2, wherein the sensitizing layer comprises a layer of antigens.

9. A sensor for assaying a plurality of substances in a sample comprising:

a substrate having a plurality of parallel grooves in a surface;

a metal layer formed outwardly from the surface of the substrate, the metal layer substantially conforming to the grooved surface of the substrate; and a plurality of substantially non-overlapping dielectric layers formed along the metal layer for suppressing reflectance of an incident light beam having a polarization component parallel to the grooves of the substrate *and a plane of incidence perpendicular to the grooves of the substrate*.

10. The sensor of claim 9, wherein each dielectric layer interacts with at least one of the plurality of substances in the sample.

11. The sensor of claim 9, further comprising a sensitizing layer formed outwardly from the plurality of dielectric layers, the sensitizing layer capable of interacting with the substance in the sample.

12. The sensor of claim 9, wherein each of the dielectric layers has a thickness of at least 50 nm.

13. The sensor of claim 9, wherein each of the dielectric layers has a thickness of at least 130 nm.

14. The sensor of claim 9, wherein a cross-sectional shape of the grooved surface of the substrate is substantially periodic.

15. The sensor of claim 14, wherein the cross-sectional shape of the grooved surface is selected from the set of sinusoidal, trapezoidal and triangular.

16. The sensor of claim 11, wherein the sensitizing layer comprises a layer of antigens.

17. A method for assaying a substance in a sample comprising the steps of:

providing a sensor having a metal diffraction grating coated with a dielectric layer;

emitting a light beam having a polarization component parallel to grooves in the metal diffraction grating *and incident within a plane perpendicular to the grooves in the metal diffraction grating*;

exposing the sensor with the light beam over a plurality of incident angles;

detecting a first diffraction anomaly angle during the first exposing step at which zero-order reflectance of the incident light changes;

interacting the sensor with the sample;

exposing the sensor a second time with a light beam over the plurality of incident angles;

detecting a second diffraction anomaly angle during the second exposing step; and determining a measure of the substance in the sample as a function of the first angle and the second angle.

18. The method of claim 17, further comprising the step of sounding an alarm when the determined measure of the substance in the sample exceeds a predetermined threshold.

19. A method for assaying a substance in a sample comprising the steps of:

providing a sensor having a metal diffraction grating having a plurality of grooves, wherein the metal diffraction is coated with a dielectric layer;

exposing the sensor with a light beam having a *polarization* component parallel to the grooves of the grating *and incident within a plane perpendicular to the grooves in the grating*, and further wherein the component propagates substantially within the dielectric layer when the sensor is exposed with the light beam at a diffraction anomaly angle;

interacting the sensor with the sample; and determining a measure of the substance in the sample as a function of a shift in the diffraction anomaly angle.

20. The method of claim 19, wherein the exposing step comprises the step of polarizing the light beam parallel to the grooves in the metal diffraction grating.

21. The method of claim 19, further comprising the step of sounding an alarm when the determined measure of the substance in the sample exceeds a predetermined threshold.

22. The method of claim 19, wherein the determining step comprises the steps of:

splitting a reflected light beam from the sensor into a first light beam having a polarization vector parallel to grooves in the metal diffraction grating and a second light beam having a polarization vector perpendicular to grooves of the metal diffraction grating, wherein the first light beam and the second light beam each have a corresponding intensity; and monitoring a ratio of the intensities of the first light beam and the second light beam.

23. A method for assaying a plurality of substances in a sample comprising the steps of:

providing a sensor having a metal diffraction grating coated with a plurality of substantially non-overlapping dielectric layers, each dielectric layer for interacting with at least one of the substances in the sample, wherein the diffraction grating has a plurality of parallel grooves;

selectively exposing at least one of the dielectric layers with a light beam at a corresponding diffraction anomaly angle *and incident within a plane perpendicular to the grooves* such that a component of the light beam having a polarization parallel to the grooves in the sensor propagates substantially within the exposed dielectric layer;

interacting the sensor with the sample; and determining a measure for each substance in the sample as a function of a shift in the diffraction anomaly angle of the corresponding dielectric layer capable of interacting with the substance.

24. The method of claim 23, further comprising the step of sounding an alarm when the determined measure of each substance in the sample exceeds a corresponding one of a plurality of predetermined thresholds.

25. A system for assaying a substance in a sample, comprising:

a sensor sensitized for interacting with the substance in the sample comprising:

a substrate having a [grooved] *plurality of parallel grooves in a* surface, a metal layer formed outwardly from the surface of the substrate, the metal layer substantially conforming to the grooved surface of the substrate, and a dielectric layer formed outwardly from the metal layer;

a light source exposing the sensor with a light beam [at an angle of incidence] *having a plane of incidence perpendicular to the grooves in the surface of the substrate*;

a detector receiving light reflected from the sensor, the detector responsive to light polarized parallel to the grooves in the surface of the substrate; and a controller coupled to the detector for calculating a measure of the substance in the sample as a function of an anomaly angle at which a change in zero-order reflectance of the light beam *occurs*.

26. The system of claim 25, wherein the sensor further comprises a sensitizing layer formed outwardly from the dielectric layer.

27. The system of claim 25, wherein the dielectric layer interacts with the substance in the sample.

28. The system of claim 25, wherein the dielectric layer has a thickness of at least 50 nm.

29. The system of claim 25, wherein the dielectric layer has a thickness of at least 130 nm.

30. The system of claim 25, wherein a cross-sectional shape of the grooved surface of the substrate is substantially periodic.

31. The system of claim 30, wherein the cross-sectional shape of the grooved surface is selected from the set of sinusoidal, trapezoidal and triangular.

32. The system of claim 26, wherein the sensitizing layer comprises a layer of antigens.

33. The system of claim 25 wherein the detector further comprises:

a polarizing beamsplitter for receiving the reflected light and splitting the reflected light into a first component and a second component, wherein the first component has a polarization vector parallel to the grooves of the substrate and the second component has a polarization vector perpendicular to the grooves of the substrate;

a first detector for receiving the first component of the reflected light, wherein the first detector has an output signal representative of an intensity of the first component; and a second detector for receiving the second component of the reflected light, wherein the second detector has an output signal representative of an intensity of the second component, wherein the controller ratios the output signal of the first detector and the output signal of the second detector, and further wherein the controller determines the anomaly angle according the ratio of the output signals.

34. The system of claim 25 wherein the light beam has a polarization parallel to the grooves in the surface of the sensor.

* * * * *